United States Patent [19]

Burns et al.

[11] Patent Number: 5,585,361

[45] Date of Patent: Dec. 17, 1996

[54] METHODS FOR THE INHIBITION OF PLATELET ADHERENCE AND AGGREGATION

[75] Inventors: James W. Burns, Boston; Cesare R. Valeri, Marblehead, both of Mass.

[73] Assignees: Genzyme Corporation, Framingham; The Trustees of Boston University, Boston, both of Mass.

[21] Appl. No.: 255,252

[22] Filed: Jun. 7, 1994

[51] Int. Cl.$^6$ .................................................. A61K 31/70
[52] U.S. Cl. ............................................. 514/25; 514/822
[58] Field of Search ..................................... 514/25, 822

[56] References Cited

U.S. PATENT DOCUMENTS

| | | | |
|---|---|---|---|
| 4,774,093 | 9/1988 | Provonchee et al. | 424/493 |
| 4,973,580 | 11/1990 | Mascellani et al. | 514/54 |
| 4,987,222 | 1/1991 | DeAmbrosi et al. | 536/21 |

FOREIGN PATENT DOCUMENTS

0557118A1  8/1993  European Pat. Off. .

OTHER PUBLICATIONS

Badimon et al., "Platelet Thrombus Formation on Collagen Type I", *Circulation*, 78:1431–1442, 1988.

Bjorck et al., "Hyaluronic Acid Sulphate Studies on Its Inhibitory Action on Platelet Function in Vitro and in Vivo", *European Society for Surgical Research. Abstracts*, 17th Congress, Stresa 1982, pp. 145–146.

Bracey et al., "Platelet Dysfunction Associated With Wilms Tumor and Hyaluronic Acid", *American Journal of Hematology*, 24:247–257, 1987.

Cofrancesco et al., "Correlation of Sulfate Content and Degree of Carboxylation of Heparin and Related Glycosaminoglycans with Anticomplement Activity. Relationships to the Anticoagulant and Platelet–Aggregating Activities", *Thrombosis Research*, 14:179–187, 1979.

Copley et al., "A Survey of Surface Hemorheological Experiments On The Inhibition of Fibrinogenin Formation Employing Surface Layers of Fibrinogen Systems With Heparins and Other Substances. A Contribution on Antithrombogenic Action", *Thrombosis Research*, 35:237–256, 1984.

Coppes, "Serum Biological Markers and Paraneoplastic Syndromes in Wilms Tumor", *Medical and Pediatric Oncology*, 21:213–221, 1993.

Danishepsky et al., "Conversion of Carboxyl Groups of Mucopolysaccharides into Amides of Amino Acid Esters", *Carbohyd. Res.*, 16:199–205, 1971.

Frost et al., "Binding of Hyaluronic Acid to Mammaliam Fibrinogens", *Biochimica et Biophysica Acta*, 1034:39–45, 1990.

Gebbink et al., "Specific Glycosaminoglycans Support the Inhibition of Thrombin by Plasminogen Activator Inhibitor 1", *Biochemistry*, 32:1675–1680, 1993.

George et al., "The Clinical Importance of Acquired Abnormalities of Platelet Function", *The New England Journal of Medicine*, 324:27–39, 1991.

Glenn et al., "Platelets, Prostaglandins, Red Cells, Sedimentation Rates, Serum and Tissue Proteins and Non–Steroidal Anti–Inflammatory Drugs", *Proceedings of the Society for Experimental Biology and Medicine*, 141: 879–886, 1972.

Kestin et al., "The Platelet Function Defect of Cardiopulmonary Bypass", *Blood*, 82:107–117, 1993.

Klein et al., "Influence of Proteoglycans (PG) and Glycosaminoglycans (GAG) on ADP–, Collagen– and Thrombin–Induced Platelet Aggregation", *Artery*, 8:410–415, 1980.

Laurent et al., "Hyaluronan", *The Faseb Journal*, 6:2397–2404, 1992.

LeBoeuf et al., "Human Fibrinogen Specifically Binds Hyaluronic Acid", *The Journal of Biological Chemistry*, 261:12586–12592, 1986.

LeBoeuf et al., "Effects of Hyaluronic Acid and Other Glycosaminoglycans on Fibrin Polymer Formation", *Biochemistry*, 26:6052–6057, 1987.

Murase et al., "Acid Mucopolysaccharides As Cofactor in Formation of Platelet –clumping Substance", *Blood*, 37:684–691, 1971.

Murata et al., "Distribution of Acidic Glycosaminoglycans in the Intima, Media and Adventitia of Bovine Aorta and Their Anticoagulant Properties", *Atherosclerosis*, 21:93–193, 1975.

Murata et al., "Effects of Acidic Glycosaminoglycans in Human Aortic Inner and Outer Layers on Partial Thromboplastin Time", *Atherosclerosis*, 29:95–104, 1978.

Nakashima et al., "Proteoglycan Obtained From Bovine Aorta Suppress Thrombin –Induced Platelet Aggregation", *Artery*, 19:256–270, 1992.

Packer et al., "Procoagulant Effects of Intraocular Sodium Hyaluronate", *American Journal of Ophthalmology*, 100:479–480, 1985.

Pandolfi et al., "The Effect of Sodium Hyaluronate and Sodium Chondroitin Sulfate on the Coagulation System in Vitro", *Ophthalmology*, 91:864 –866, 1984.

Scully et al., "The Antiheparin effect of a Heparinoid, Pentosan Polysulphate. Investigation of a Mechanism", *The Biochemical Journal*, 218:657–665, 1984.

Sobel et al., "Characterization of Platelet Binding of Heparins and Other Glycosaminoglycans", *Thrombosis Research*, 50:815–826, 1988.

Sparer et al., Chap. 6, "Controlled Release from Glycosaminoglycan Drug Complexes", pp. 107–119 In *Controlled Release Delivery Systems*, Roseman et al. (ed.), Marcel Dekker, Inc. : NY, 1983.

Waldenstrom et al., "Accumulation of Hyaluronan and Tissue Edema in Experi mental Muocardial Infarction", *The Journal of Clinical Investigation*, 88:1622–1628, 1991.

(List continued on next page.)

*Primary Examiner*—Kimberly Jordan
*Attorney, Agent, or Firm*—Fish & Richardson P.C.

[57] ABSTRACT

Methods of preventing or treating thrombotic conditions by administering pharmaceutical compositions containing hyaluronic acid are described.

32 Claims, 13 Drawing Sheets

OTHER PUBLICATIONS

Weigel et al., "A Model for the Role of Hyaluronic Acid and Fibrin in the Early Events During the Inflammatory Response and Wound Healing", *J. Theor. Biol.*, 119:219–234, 1986.

Weigel et al., "The Specific Interaction Between Fibrin(ogen) and Hyaluronan: Possible Consequences in Haemostasis, Inflammation and Wound Healing", *The Biology of Hyaluronan*. Wiley, Chicester (Ciba *Foundation Sumposium*143), pp. 248–264, 1989.

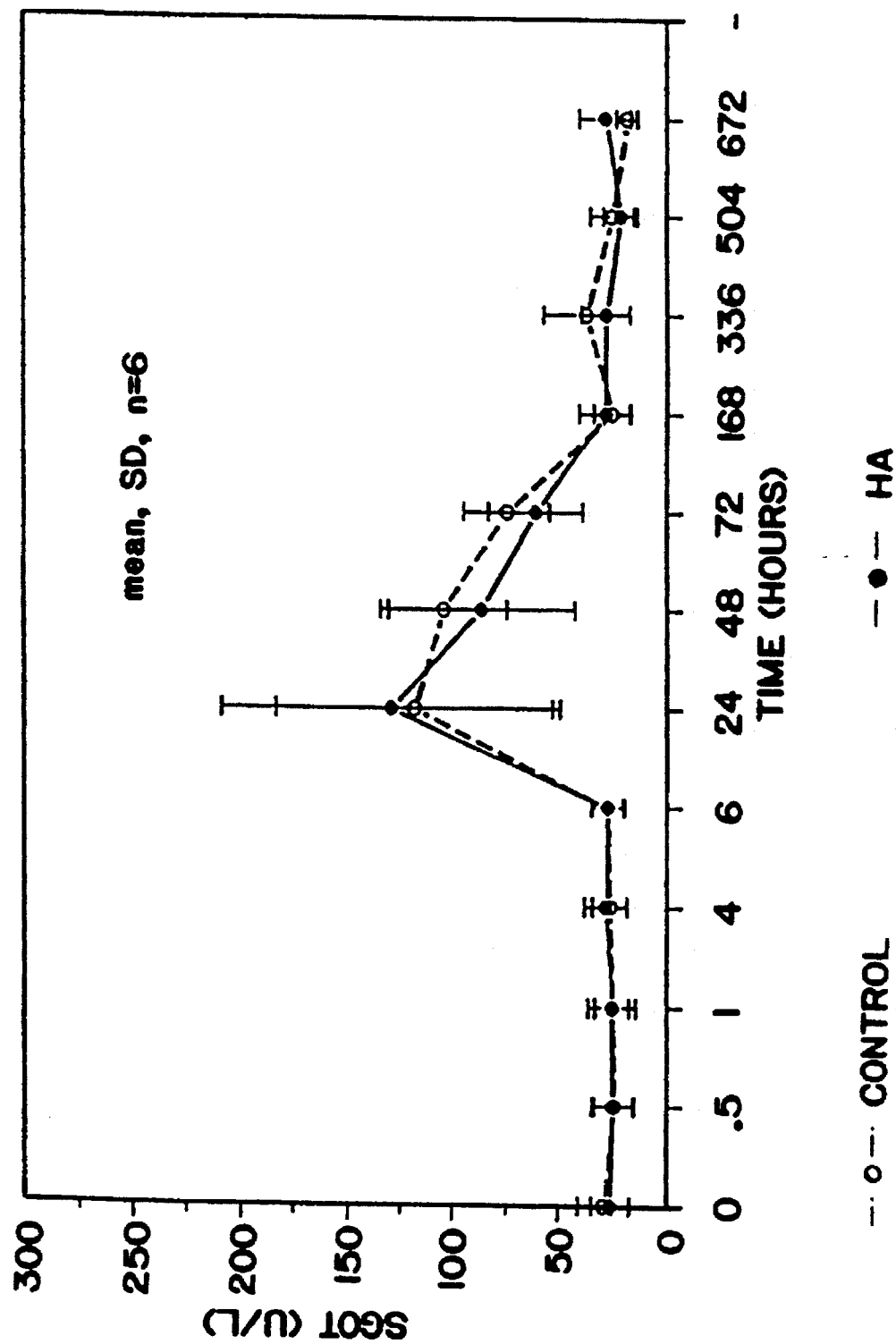

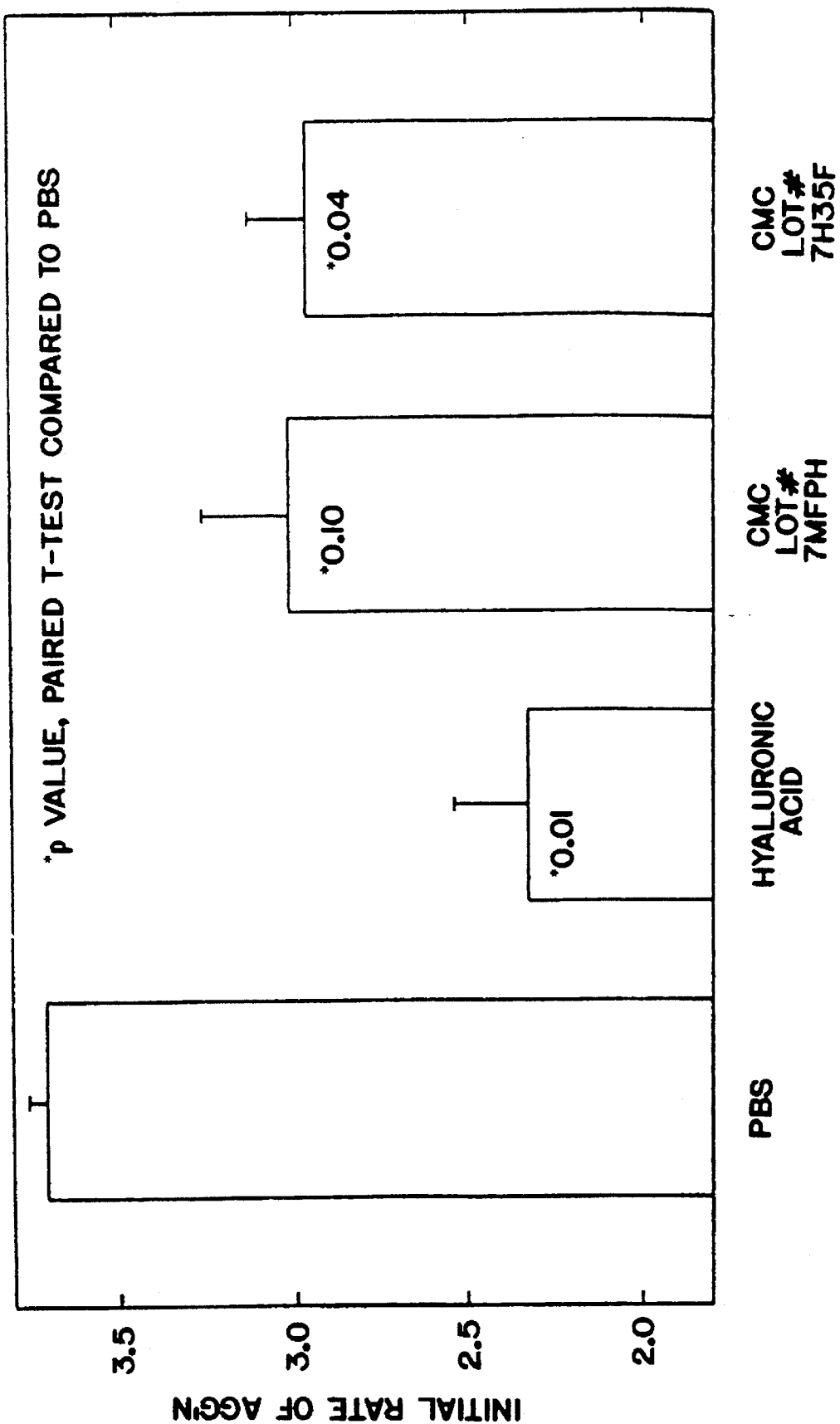

METHODS FOR THE INHIBITION OF PLATELET ADHERENCE AND AGGREGATION

This invention was made with Government support under contract N00014-88-C-0118 awarded by the Department of the Navy. The Government has certain rights in the invention.

The invention relates to the inhibition of platelet adherence and aggregation via the administration of hyaluronic acid.

BACKGROUND OF THE INVENTION

When a blood vessel is damaged and the normal endothelial-cell barrier is disrupted, platelets are quickly recruited from the circulating blood to form an occlusive plug. This occurs through a series of interactions between the platelets and macromolecules in the subendothelial matrix (platelet adhesion) and among the platelets themselves (platelet aggregation). The initial process of adhesion, in contrast to aggregation, does not require metabolic activity. It leads, however, to the activation of platelets which in turn secrete a number of factors which stimulate the activation of plasma coagulation factors, resulting in the generation of a fibrin clot that reinforces the platelet aggregate. Under normal hemostatic condition the platelet aggregate and fibrin clot are degraded as healing of the injured area occurs.

Thrombosis is a pathological process in which a platelet aggregate and/or fibrin clot occlude a blood vessel. Venous thrombosis and pulmonary embolism are among the leading causes of morbidity and death in hospitalized patients. Studies with radioactively labeled fibrinogen reveal venous thrombi in the lower legs of about one fourth of all patients older than 50 years who have undergone routine inguinal herniorrhaphy, in more than one half of all prostatectomy or hip surgery patients, and in about one third of all patients with acute myocardial infarction. Predisposing factors include posttraumatic and postoperative immobility (particularly in middle-aged and elderly patients and after cardiovascular procedures), pregnancy, previous episodes of venous thrombosis, use of oral contraceptives, stroke, neoplasia, obesity, systemic lupus erythematosus, nephrotic syndrome, polycythemia vera, inflammatory bowel disease, homocystinuria, hyperhomocysteinemia, paroxysmal nocturnal hemoglobinuria, shock, and congestive heart failure.

Thrombosis that develops as a purely intravascular process may also be the primary factor in atherosclerosis. The formation of platelet aggregates on the surface of atheromatous plaques and subsequent organization of these white thrombi into fibrous occlusive intimal lesions in undoubtedly one mechanism by which atherosclerotic lesions progress to severe obstruction and total occlusion; coronary artery thrombosis leading to myocardial infarction almost always occurs at the site of an atheromatous plaque. Percutaneous transluminal coronary angioplasty (PTCA) has become an important procedure to re-establish blood flow to the heart through partially occluded blood vessels. Unfortunately approximately 30% to 40% of patients that have coronary angioplasty suffer restenosis of the treated vessel within 6 months of treatment; currently there is no reliable method of preventing vascular restenosis. A revascularization procedure such as bypass surgery or another PTCA procedure is thus often required.

Current therapies for the prevention and treatment of thrombus formation associated with various disease states and surgical procedures have focused primarily on the use of the anticoagulants heparin or warfarin. Most commonly, basic therapy usually involves immediate heparinization which may be followed by long-term administration of warfarin if there is a prolonged risk of thrombus reoccurrence.

Heparin prevents the release of serotonin and thromboxane $A_2$ from platelets. These vasoactive substances are suspected mediators of the intense pulmonary artery hypertension, acute right-side hemodynamic failure, and cardiogenic shock associated with pulmonary embolism. Heparins' rapid action in preventing thrombus propagation and in blocking platelet release is the rationale for its use. However, a frequent complication of heparinization is major bleeding (usually after 48 hours); such bleeding is especially hazardous if it occurs intracranially. The risk of bleeding is dose related and is higher in woman, in severely ill patients, in individuals who consume large amounts of alcohol, and in individuals who take heparin and aspirin concurrently. Although the action of heparin may be terminated by intravenous injection of protamine sulfate, the use of protamine has been linked to several post-surgical complications, including postoperative systemic hypotension, allergic reactions, catastrophic pulmonary vasoconstriction, acute pulmonary hypertension, complement activation, noncardiogenic pulmonary edema, decreased cardiac output, and thrombocytopenia/leukopenia. Since protamine, usually isolated from fish, can be recognized as a foreign protein by the human immune system, patients with prior protamine exposure (e.g., diabetic patients who have received protamine insulin) are at particular risk during subsequent exposures (Just Viera, *Amer. Surgeon* 50:151, 1984). Additionally, studies suggest that a non-immunological pathway via complement activation may be responsible for many of the acute reactions observed during protamine reversal of heparin anticoagulation.

Warfarin interferes with the γ-carboxylation of glutamic acid residues in the vitamin K-dependent synthesis of factors II, VII, IX, and X in liver mitochondria. The drug is completely absorbed and is predominantly protein-bound in the plasma, where its half-life is 42 hours. It is degraded in the liver and its metabolites, which are inactive, are excreted in the urine and stool. However, warfarin will not affect procoagulant proteins already formed in the liver and released into the circulation, and the half-life of some of these factors is longer than 24 hours, thus delaying the anticoagulant effects of this drug for several days. In addition, a number of drugs interact significantly with warfarin, and hereditary resistance to warfarin exists as an autosomal dominant trait in some families.

If heparinization is ineffective to stop progression of thrombus formation, or in the cases where occlusion is acute and life threatening, thrombolytic therapy is usually used. Three thrombolytic agents are currently used; urokinase, which is harvested from human fetal kidney cells and cleaves plasminogen to plasmin; streptokinase, which is derived from streptococci and complexes with and activates plasminogen; and recombinant tissue plasminogen activator (rtPA). These agents may hasten thrombus dissolution, but they also lyse hemostatic fibrin and may cause hemorrhaging. Thus, concurrent use of these thrombolytic agents with heparin or warfarin is usually avoided. In addition, the nonrecombinant agents are pyrogens and potential allergens, especially streptokinase, which has been associated with anaphylaxis.

Although venous thrombosis during pregnancy is common, and pulmonary embolism is a leading cause of maternal mortality, anticoagulant therapy during pregnancy poses significant therapeutic problems. Warfarin crosses the placenta and affects the fetus, in addition to being associated with hemorrhagic complications. Embryopathy (nasal hypoplasia, altered bone growth, and stippled epiphyses) has been clearly attributed to coumarin derivatives; the critical period for exposure appears to be between the sixth week and the twelfth week of gestation. Far less common are such serious fetal central nervous system abnormalities as mental retardation, blindness, deafness, spasticity, and seizures. These defects appear to be unrelated to any critical period of exposure and may be associated with warfarin administration during the second and third trimesters. Various congenital ocular abnormalities have also been reported after warfarin therapy.

Heparin does not cross the placenta, and currently, adjusted-dose heparin is the preferred anticoagulant used during pregnancy complicated by venous thromboembolism. However, in one study, about one-eighth of the pregnancies treated with heparin ended in stillbirth, and one fifth of the mothers gave birth to premature infants, one third of whom died. Other problems associated with heparin administration during pregnancy include retained placenta, premature detachment of the placenta and minor hematomas.

SUMMARY OF THE INVENTION

We have discovered that hyaluronic acid is capable of interfering with the interaction of yon Willebrand factor (vWF) with platelets and components of the subendothelial matrix to effectively inhibit platelet aggregation and adhesion. Accordingly, this discovery permits the use of hyaluronic acid for the inhibition of platelet adherence and aggregation in a number of disease states which are or can be pathological.

In one aspect, the invention features a method of treating a thrombotic condition in a mammal, preferably a human, by administering to the mammal a therapeutic composition containing hyaluronic acid in a dosage effective to inhibit the adherence and aggregation of platelets within the mammal's vascular system.

In one preferred embodiment of this aspect, the thrombotic condition is venous thrombosis, particularly venous thrombosis which can lead to the development of pulmonary emboli (e.g., iliofemoral thrombosis, mesenteric vein thrombosis and Budd-Chiari syndrome). The method is especially useful in treating venous thrombosis during pregnancy.

In another preferred embodiment of this aspect, the thrombotic condition is arterial thrombosis, particularly coronary artery thrombosis.

In a second aspect, the invention features a method of preventing the formation of a thrombus in a mammal at risk of developing thrombosis by administering to the mammal a therapeutic composition containing hyaluronic acid in a dosage effective to inhibit the adherence and aggregation of platelets.

In one preferred embodiment of this aspect, the mammal is at increased risk of developing a thrombus due to a medical condition which disrupts hemostasis, including heparin induced thrombocytopenia, coronary artery disease, atherosclerosis, pregnancy, stroke, neoplasia, obesity, systemic lupus erythematosus, nephrotic syndrome, polycythemia vera, inflammatory bowel disease, homocystinuria, hyperhomocysteinemia, paroxysmal nocturnal hemoglobinuria, shock, and congestive heart failure.

In another preferred embodiment of this aspect of the invention, the mammal is at increased risk of developing a thrombus due to a medical procedure, including cardiac surgery, cardiopulmonary bypass, catheterization, cardiac catheterization, percutaneous transluminal coronary angioplasty, atherotomy. Also included are procedures which involve the placement of either a synthetic or bioprosthetic prosthesis (e.g., a cardiovascular valve).

In both of these aspects of the invention, HA may be administered systemically or locally. The administration of HA may occur prior to, during, or after a medical procedure, or treatment with other agents (e.g., thrombolytic agents).

In still another aspect, the invention also features a method of inhibiting the adherence of platelets to the surface of a prosthetic device by coating the device with hyaluronic acid in an amount sufficient to inhibit the interaction of the platelets with the surface of the device prior to exposure of the device to the platelets.

The device can be made of any suitable biocompatible material, either totally or partially synthetic, that is commonly used in medical procedures. In preferred embodiments, the prosthetic device is a coronary valve, vascular graft, or a stent.

Also in preferred embodiments of the invention, the HA solution concentration for systemic administration in the blood to prevent platelet adhesion is in the range of 0.1% to 0.4% (weight percent) and is administered in an amount greater than approximately 5% of the total blood volume of the patient and less than 15%. The viscosity of the HA solution should be less than 1000 centipoise and greater than 20 centipoise. The molecular weight of the HA can be adjusted according to the desired viscosity for a specific HA concentration. Preferably the average molecular weight of the HA is greater than $1 \times 10^5$ daltons; more preferably, between $2.25 \times 10^5$ and $2.0 \times 10^6$; and even more preferably, between $7.0 \times 10^5$ and $2.0 \times 10^6$.

For the local administration of HA solution at the site of intended action to prevent platelet adhesion, the HA concentration can be from 0.1% to 5.0% with an HA solution viscosity that ranges from 20 centipoise to 300,000 centipoise.

Molecular weights of HA can be determined by light scattering measurements as described in Yu L. P. et al., "Rheological Characteristics of Microbially Derived Sodium Hyaluronate", American Chemical Society Proceedings Series—Harnessing Biotechnology for the 21 st Century, M. R. Ladisch and R. Bose eds., p 80–84, 1992.

Viscosity as described herein can be determined with a Brookfield cone and plate viscometer using the lowest shear rate that yielded results greater than 10% full scale.

As used herein, the term "HA" means hyaluronic acid and any of its hyaluronate salts, including, for example, sodium hyaluronate, potassium hyaluronate, magnesium hyaluronate, and calcium hyaluronate.

The term "platelet aggregation" as used herein means the amassing together of individual platelets through specific interactions between platelets.

The term "platelet adhesion" as used herein means the amassing of platelets onto a surface (e.g., a vascular wall, prosthetic device) through interactions of the platelets with the surface.

The terms "restenosis" and "reocclusion" as used herein mean the narrowing or constriction of the diameter of a vessel or duct.

The term "systemic" administration as used herein means to administer a substance at a substantial distance from the site where the substance is intended to act, usually by intravenous administration.

"Local administration", as used herein, refers to the contacting of a therapeutic agent, i.e., HA, in the immediate proximity of the tissue in the body where its therapeutic effect is desired.

Unless defined otherwise, all technical and scientific terms used herein have the same meaning as commonly understood by one of ordinary skill in the art to which this invention belongs. Although any method and materials similar or equivalent to those described herein can be used in the practice or testing of the present invention, the preferred methods and materials are now described. All publications mentioned hereunder are incorporated by reference. Unless mentioned otherwise, the techniques employed or contemplated herein are standard methodologies well known to one of ordinary skill in the art. The materials, methods and examples are illustrative only and not intended to be limiting.

Our studies show that HA can be used to effect platelet adhesion and aggregation in a specific manner without interfering with other hemostatic events, unlike heparin and warfarin. For example, prior to the present invention, one common method of preventing vessel reocclusion following PTCA procedures is to place a stent device at the site of angioplasty in order to maintain the vessel patency and to administer heparin to reduce platelet adhesion to the stent. However, heparin has many effects on coagulation which are not always desirable in a vascular compromised state; heparin interferes with thromboxane production which is a potent regulator of normal platelet function, and heparin also has fibrinolytic activity which will induce lysis of clots in the general circulation.

In contrast, the methods of the invention may be practiced to decrease the risk of pathological thrombus formation associated with a diseased state or any medical procedure including cardiovascular surgery, cardiopulmonary bypass, catheterization (e.g., cardiac catheterization, or angioplasty) with a substantially reduced risk of affecting overall hemostasis. Further, HA will be especially useful in the cases where heparin and/or warfarin treatment may not be used, e.g., patients demonstrating protamine allergy, heparin induced thrombocytopenia, and warfarin resistance, as well those who are being treated with drugs which are incompatible with warfarin, or who are pregnant.

Other features and advantages of the invention will be apparent from the following description and from the claims.

DETAILED DESCRIPTION

Drawings The drawings will first be briefly described.

FIG. 11 is a graphic representation of the effect of HA infusion on serum SGOT.

FIG. 13 is a bar graph depicting the effects of HA and CMC on ristocetin induced platelet aggregation.

Figure 1:
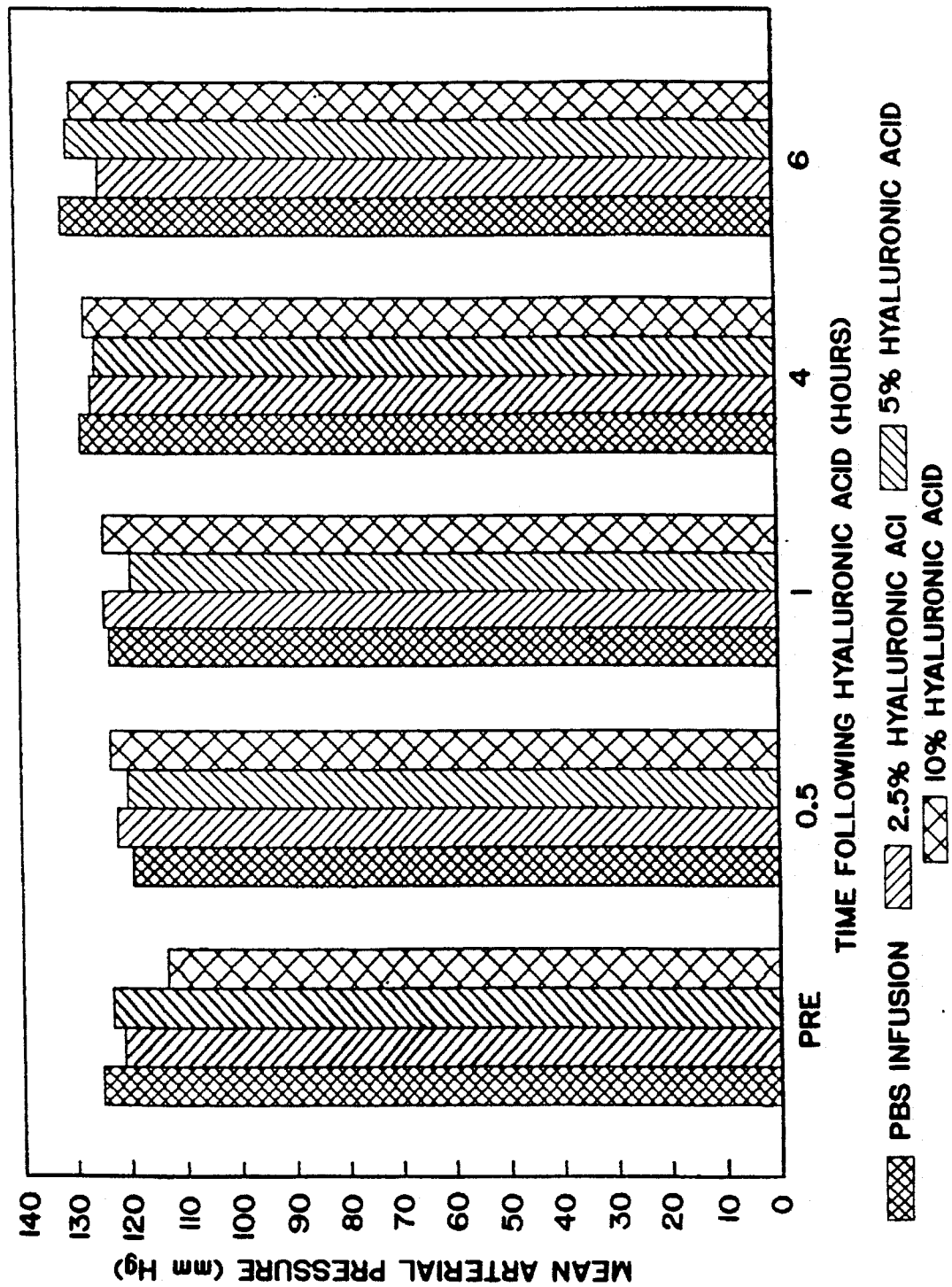
FIG. 1 is a bar graph depicting the effect of HA infusion on arterial pressure.

Hyaluronic acid (HA) is a component of the extracellular matrix in mammals that has been conserved throughout evolution. This mucopolysaccharide is a linear polymer built from repeating disaccharide units with the structure . . . [D-glucuronic acid(1-β-3) N-acetyl-D-glucosamine (1-β-4)] n. It is ubiquitous within the human body, and is found in a wide range of forms as a normal constituent in a variety of tissues including synovial fluid, vitreous humor, blood vessel walls, pericardial fluid, and umbilical cord.

Hyaluronic acid is present in blood in low concentrations. It comes from the peripheral tissues via the lymph (Laurent et al., *Biochem. Int.* 2:195, 1981). From the concentration of hyaluronic acid in blood and its turnover rate as measured by labeled tracers, it has been estimated that a total amount of 10–100 mg turned over in the circulation of an adult human every day (Fraser et al., In *The Biology of Hyaluronan*, Ciba Foundation Symposium 143:41–59, Wiley, Chichester, England).

Dilute solutions of hyaluronic acid, in addition to being nonantigenic, are extremely lubricous, even at very low concentrations. HA solutions have been shown to reduce postoperative adhesion formation following abdominal (Urman et al., *Fertil Steril* 56:563, 1991) and orthopedic surgery (Hagberg et al., *J Hand Surg* 17A:935, 1992).

In addition to its anti-adhesion effects, HA solutions have been used clinically in ophthalmologic, orthopedic, and oral/maxillofacial surgery due to the unique viscoelastic properties of the material. Because of the high viscosity, administered HA solutions are retained in the anterior chamber of the eye and serve to protect fragile corneal endothelial surfaces during intraocular lens implantation (Pape et al., *Ophthalmology* 87:699, 1980). Injected into the joint space, HA solutions act as lubricants to provide pain relief in those with osteoarthroses (Iwata, *Clin Orthop* 289:285, 1993) and certain temporomandibular joint disorders (Bertolami et al., *J Oral Maxillofac Surg* 51:232, 1993). Interestingly, topical HA solutions have also been shown to be beneficial in the healing of tympanic membrane perforations (Hellstrom et al., *Acta Otolaryngol* 442:54, 1987).

The experiments described below describe the effect of HA on the function to inhibit platelet aggregation and adherence.

The Effect of HA on Bleeding Time

This study was designed to assess the effect of a large parenteral infusion of 0.4% HA in PBS ($1.5 \times 10^6$ to $2.0 \times 10^6$ daltons), equivalent to either 2.5%, 5%, or 10% of the animal's measured blood volume. Hemodynamic, gas exchange, hematologic, and coagulation parameters were evaluated as described below. A separate infusion of PBS alone, equivalent to 10% of the blood volume in each animal, served as a control. Healthy male baboons (n=6) were used in this study, weighing between 27 and 36 kg (mean 30.2 kg).

Experimental Protocol

Approximately one week prior to study, each baboon's red cell volume was measured with $^{51}$Cr labeled autologous red blood cells, and the plasma volume was measured using $^{125}$I labeled albumin. Using this data, infusate volumes equivalent to 2.5%, 5%, and 10% of the circulating blood volume in each animal were determined. Each animal served as its own control and was thus studied on four occasions: once following infusion of PBS in a dose equal to 10% of the blood volume (control), and after infusions of test material doses equal to 2.5%, 5%, and 10% of the total blood volume. The order in which the control and test infusions were given was randomized. On the initial study day for each infusion, the animals were anesthetized with intramuscular ketamine (4 mg/kg), repeated as needed to maintain anesthesia. The right femoral artery was cannulated for mean arterial pressure measurement. A flow-directed pulmonary arterial thermodilution catheter was placed via the right internal jugular vein for measurement of central venous pressure, mean pulmonary arterial pressure, mean pulmonary arterial wedge pressure, and cardiac output. After a steady state was achieved baseline samples were taken, followed by intravenous infusion of either the test or control material over a fifteen minute period. Sampling was done prior to infusion and 0.5, 1, 4, and 6 hours and 1, 2, 3, 7, 14, 21, and 28 days following infusion.

Hematocrit, hemoglobin, red blood cell count, white blood cell count, platelet count, and mean platelet volume were measured using an automated cell counter (Model JT, Coulter Corp., Hialeah, Fla.) for each time point as described above. Whole blood viscosity was measured using a porous bed viscometer (Crowley et al., *Am J Clin Pathol* 96:729, 1991). Blood pH, $PO_2$, $PCO_2$, sodium, potassium, ionized calcium, % O2 hemoglobin, % CO hemoglobin, volume % O2, and methemoglobin were measured using an automated blood gas analyzer (NovaStat Profile 4, Nova Biomedical, Waltham, Mass.). Mean arterial pressure, central venous pressure, mean pulmonary artery pressure, and mean pulmonary artery wedge pressure were measured by placement of a catheter into each of the femoral and pulmonary arteries. Bleeding time was measured by making a standard incision using a Simplate II bleeding time device (Organon Technika, Oklahoma City, Okla.). Core temperature was assessed in the pulmonary artery on the day of the study, and in the esophagus on the post-infusion days 1 through 28 using a pulmonary artery catheter placed in the esophagus. Skin temperature of the forearm was measured using a thermocouple (Mon-A-Therm) and an infra-red laser scanner (Exergen). Lung function was assessed by measuring respiration rate, and the $pO_2$, $pCO_2$ and volume of expired air. Expired air was collected in Douglas bags and $pO_2$ and $pCO_2$ were measured using a Nova Stat Profile 4 instrument. Urine output was monitored throughout the study and urine samples were frozen for subsequent measurement of BUN and creatinine. Red blood cell p50 was measured using a Hemoxanalyzer.

In addition, a portion of the blood samples obtained at each time point was frozen for later measurement of a number of criteria. Prothrombin time, partial thromboplastin time, thrombin time and fibrinogen were measured using an automated clotting machine (Coag-A-Mate, Organon Technika) (Feingold et al., *Am J Vet Res* 47:2197–2199, 1986). Antithrombin III (Helena Laboratories) was measured using a chromogenic assay (Abildgaard et al., *Thromb Res* 11:549–553, 1977). Protein C was measured by a chromogenic assay supplied by America Bioproducts Co.(Nicham et al., *CBS* 65:25). von Willebrand's factor and D-dimer levels were measured using ELISA assays (supplied by American Bioproducts Co.; Ness et al., *Thromb Haemost* 42:848, 1979; Rylatt et al., *Thromb Res* 31:767, 1983). Fibronectin was measured using an immunoturbidimetric assay (supplied by Boehringer Mannheim Biochemicals; Saba et al., *J Lab Clin Med* 98:482, 1981). Serum and urea nitrogen (BUN) and creatinine, total protein, albumin, lactic dehydrogenase (LDH), alanine aminotransferase (SGPT), and aspartate aminotransferase (SGOT) were measured using an automated chemistry analyzer (Beckman Instruments Inc., Brea, Calif.). C3a and C5a dys Arg were measured using radioimmune assays (supplied by Amersham Corp.; Chenoweth et al., *N Engl J Med* 304:497, 1981). The thromboxane B2 level in the blood shed from the arm during the bleeding time measurement was determined by radioimmune assay (supplied by New England Nuclear Corp.). Red blood cell ATP and DPG were measured using a Farrand fluorometer (Lamprecht et al., In *Methods of Enzymatic Analysis*. HU Bergmeyer (ed), pp. 543–558, New York: Academic Press; Keitt, *Am J Med* 41:762–785, 1966).

Statistical Analysis

Data were examined using one-way analysis of variance (ANOVA) with repeated measures and Student-Newman-Keuls test. Statistical significance was achieved at $p<0.05$. The results of the statistical analyses are displayed in tables 1–9.

2.5% and 5% Groups

The infusion of 0.4% HA in PBS in volumes equivalent to 2.5% and 5% of the baboon's measured blood volume had no significant effect on any of the measured parameters compared to the control infusion.

10% Group

Figure 2:
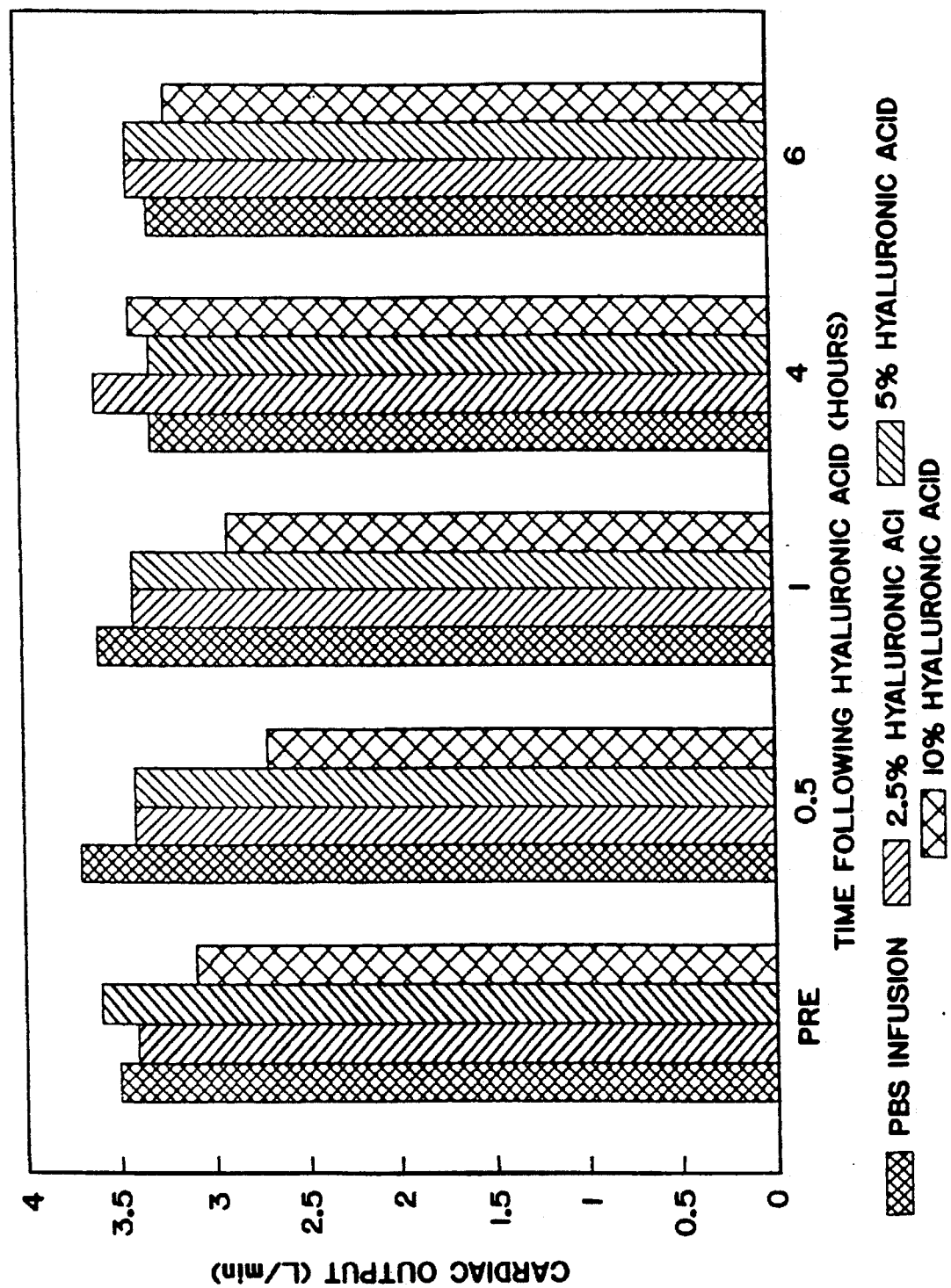
FIG. 2 is a bar graph depicting the effect of HA infusion on cardiac output.
Figure 3:
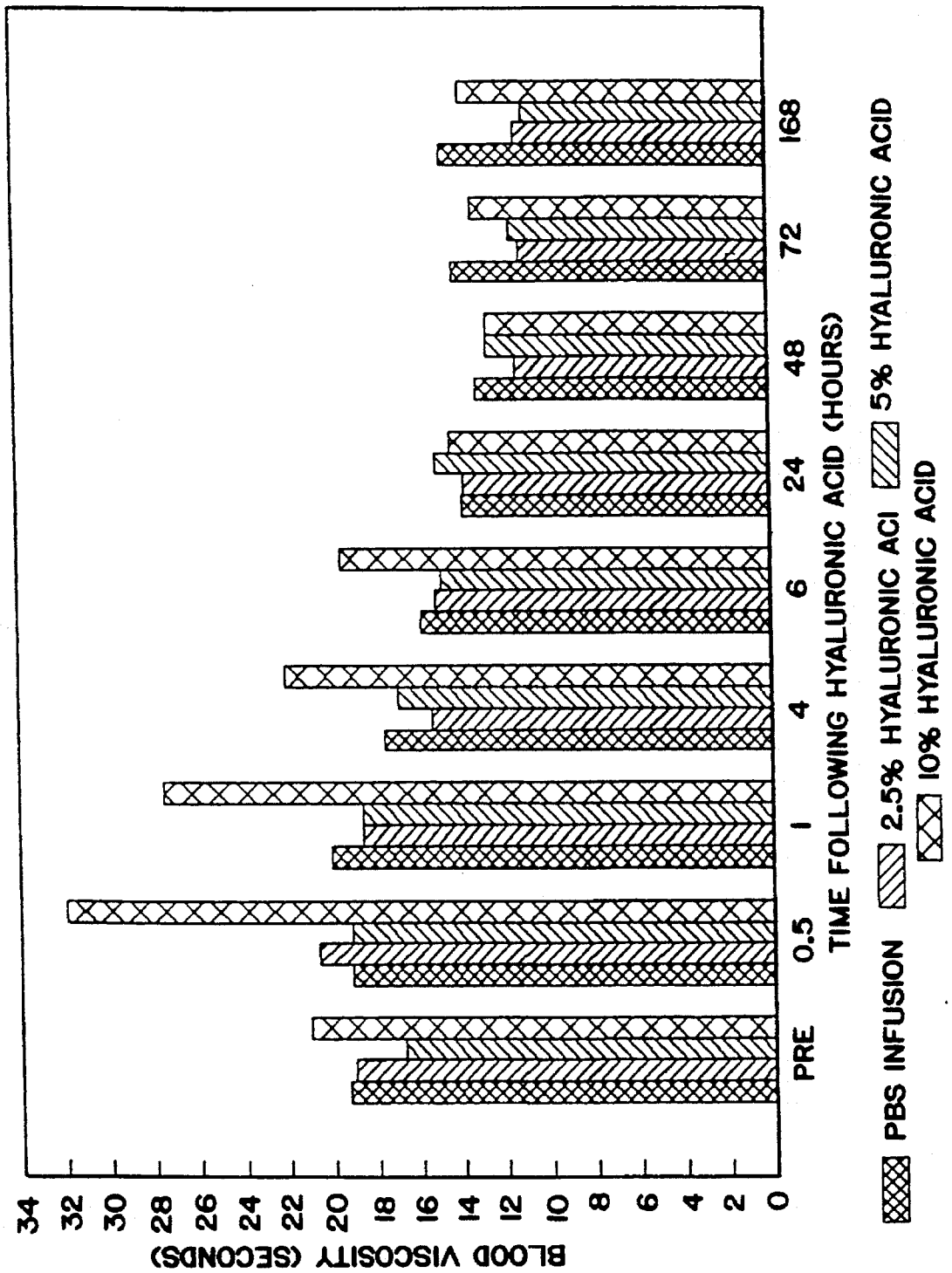
FIG. 3 is a bar graph depicting the effect of HA infusion on blood viscosity.
Figure 4:
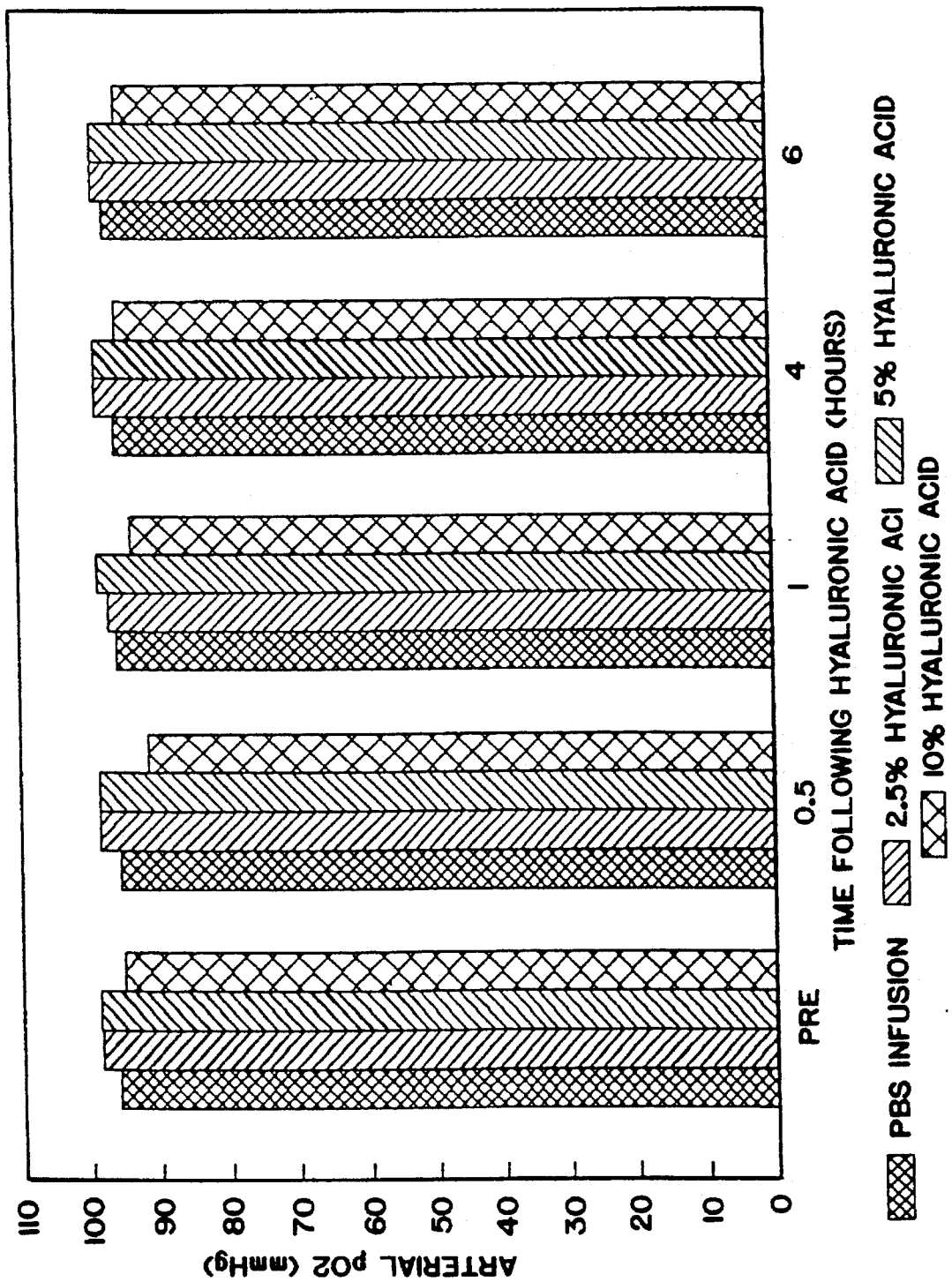
FIG. 4 is a bar graph depicting the effect of HA infusion on arterial $O_2$.
Figure 5:
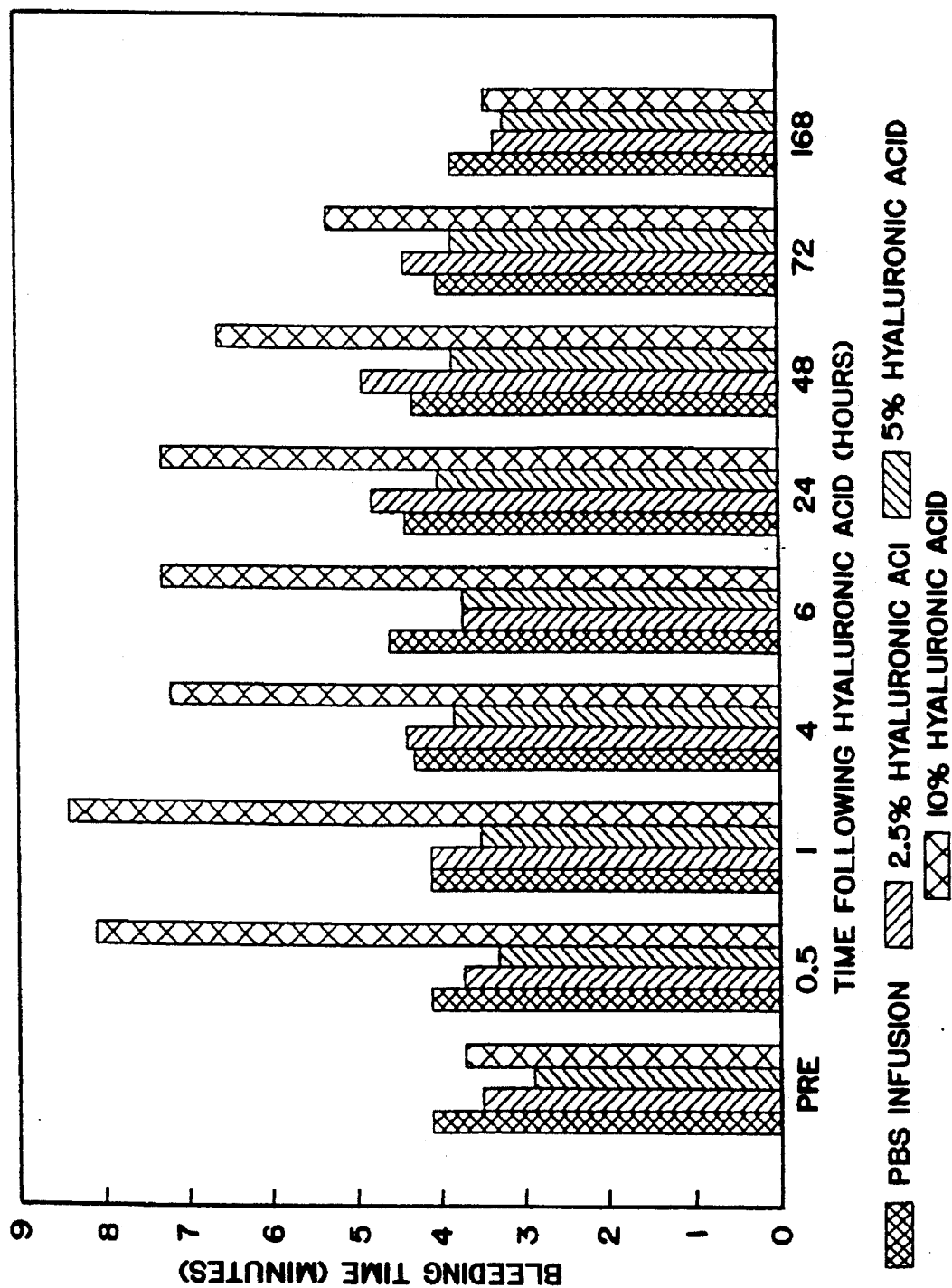
FIG. 5 is a bar graph depicting the effect of HA infusion on bleeding time.

Following infusion of a 0.4% HA solution in an amount equivalent to 10% of the circulating blood volume, there were no significant changes in central venous pressure, heart rate, or pulmonary arterial pressure. These animals did have a significant increase in mean arterial pressure in the first 30 minutes following infusion (+10% change), a finding not observed in the controls (FIG. 1). Cardiac output decreased significantly (−13% change) in the first hour, which returned to baseline within 4 hours (FIG. 2). There was a corresponding increase in blood viscosity (+52% change), systemic vascular resistance (+26% change) and pulmonary vascular resistance (+34% change), gradually returning to pre-infusion levels within 4–6 hours (FIG. 3). Arterial $O_2$ and venous $pO_2$ were significantly lower in the baboons infused with 10% HA/PBS (FIG. 4). The hematocrit, while cell count, and platelet count were not changed following infusion. However, the bleeding time significantly increased in the 10% group, to a level twice that of controls. This remained elevated for 72 hours post-infusion (FIG. 5).

Figure 6:
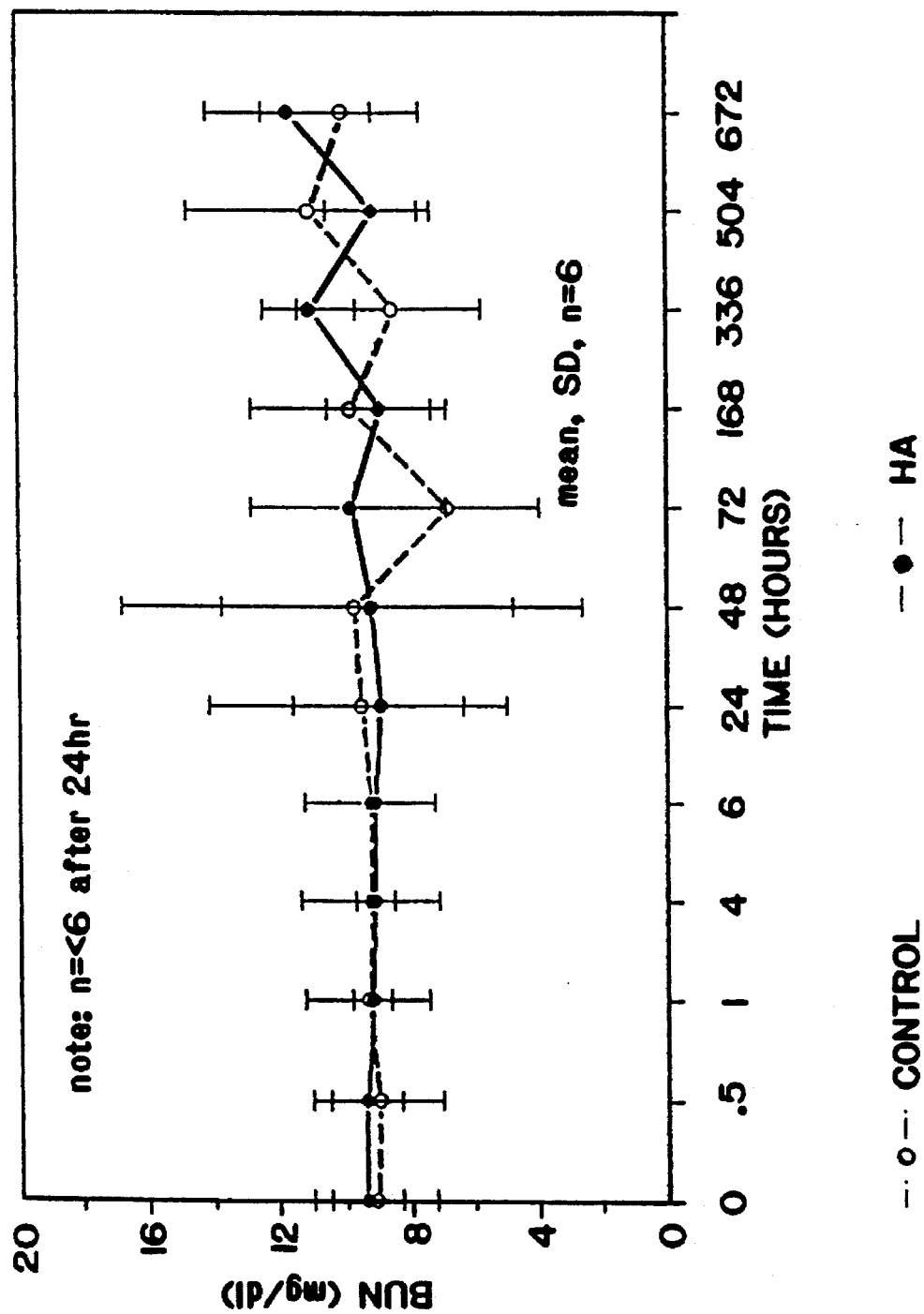
FIG. 6 is a graphic representation of the effect of HA infusion at 10% of blood volume on serum BUN values.
Figure 7:
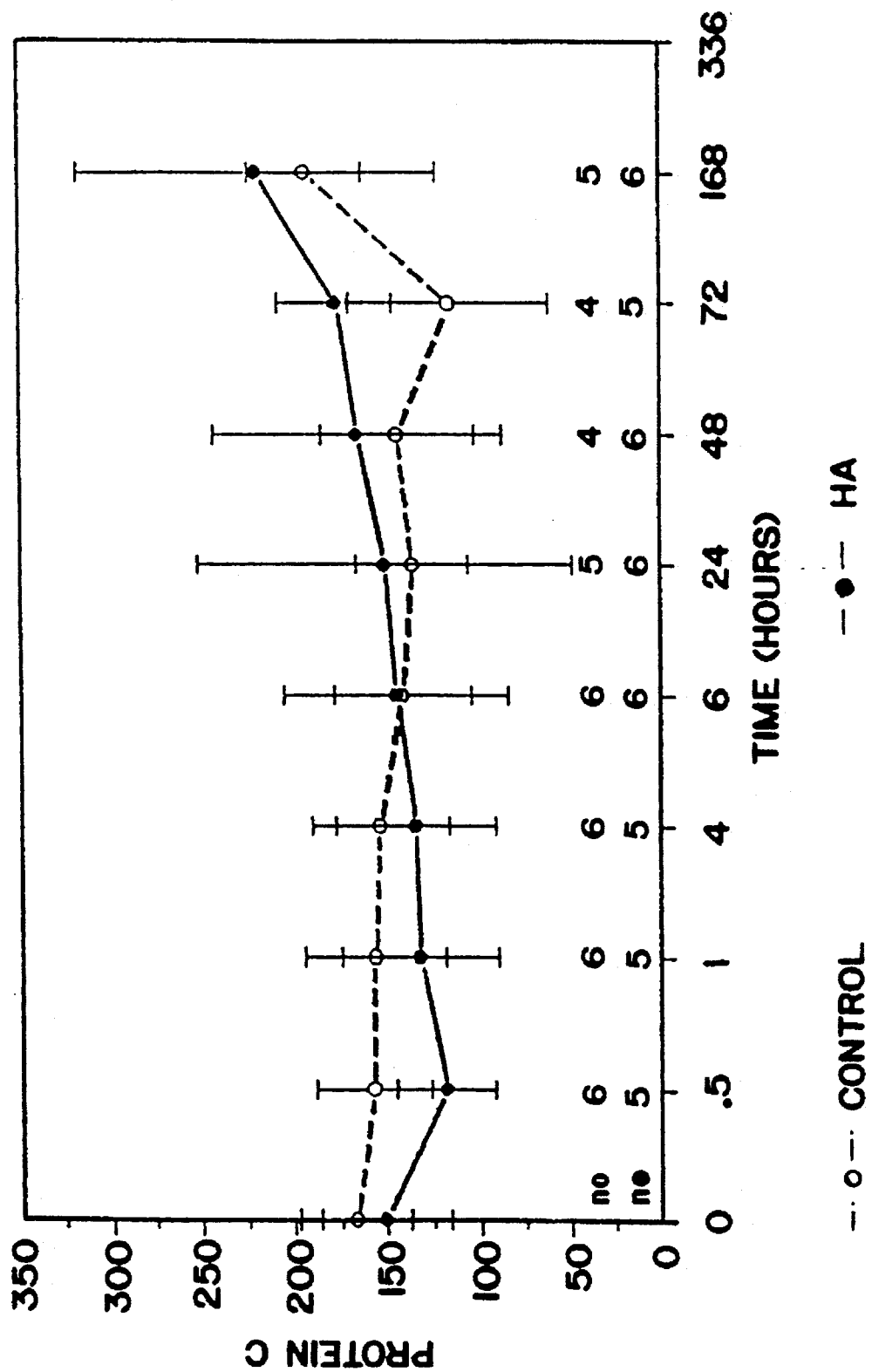
FIG. 7 is a graphic representation of the effect of HA infusion on Protein C levels.
Figure 8:
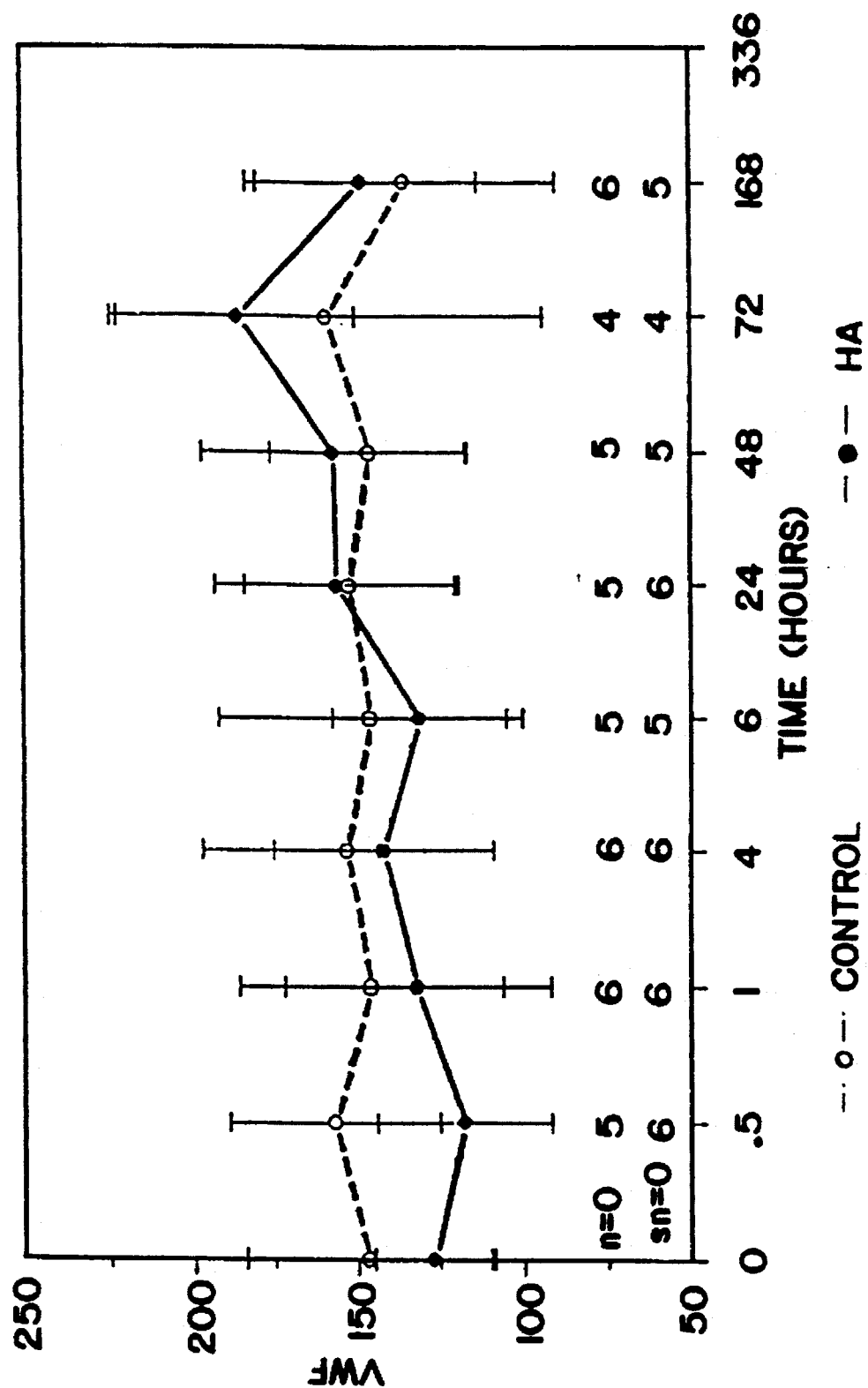
FIG. 8 is a graphic representation of the effect of HA infusion on VWF levels.
Figure 9:
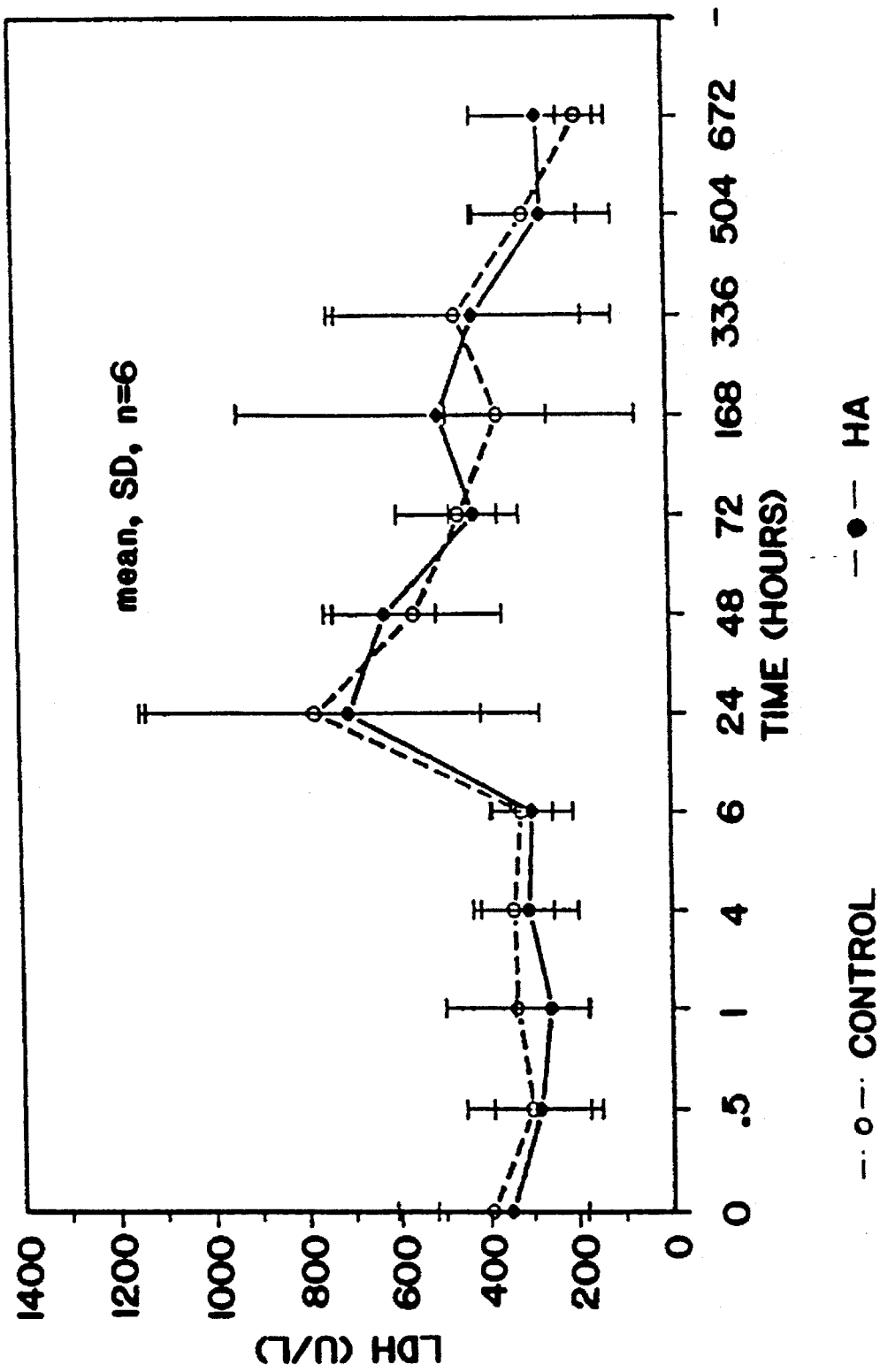
FIG. 9 is a graphic representation of the effect of HA infusion on serum LDH.
Figure 10:
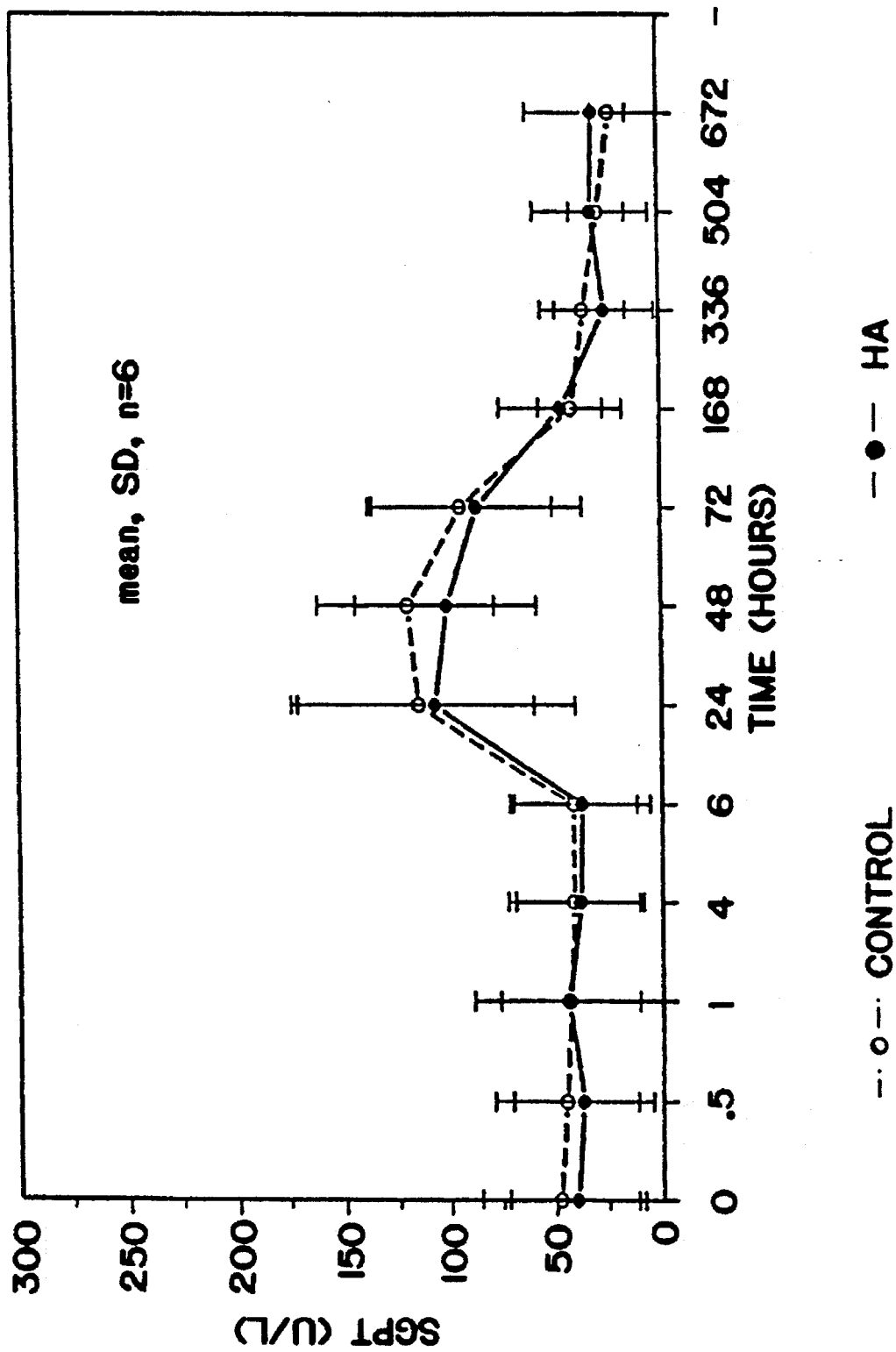
FIG. 10 is a graphic representation of the effect of HA infusion on serum SGPT.

Serum BUN and creatine values measured up to 48 hours following infusion were similar for baboons infused with PBS alone or 10% HA/PBS (FIG. 6). The prothrombin time, partial thromboplastin time, thrombin time, fibrinogen levels were not significantly changed. Protein C level and von Willebrand factor were significantly lower in the baboons infused with HA/PBS (FIGS. 7 and 8). Red blood cell p50, red cell ATP, and red blood cell 2,3 DPG activities were unchanged in the animals treated with 10% HA/PBS when compared to controls. In addition, total protein, albumin, SGOT, SGPT, and LDH were unchanged by the 10% infusion (FIGS. 9, 10, and 11).

HA is a normal constituent of serum and is rapidly catabolized within the intravascular space, with a half-life of only a few minutes (Laurent et al., *FASEB J* 6:2397, 1992). This may explain why infusion of the 0.4% HA solution equivalent to 2.5% or 5% of the circulating blood volume did not have a demonstrable effect on the various parameters measured. The clearance of HA can be described by Michaelis-Menton kinetics (Laurent et al., supra), and infusion of the 10% volume may briefly exceed the maximal metabolic rate ($V_{max}$), resulting in a transient increase in blood viscosity. Although whole blood viscosity is usually dependent on the prevailing hematocrit, changes in viscosity in the setting of a stable hematocrit (and arterial $O_2$ content) can cause independent changes in cardiac output and systemic vascular resistance (Murray et al., *Am J Physiol* 216:638, 1969). In addition, similar to whole blood, solutions containing HA act in a non-Newtonian fashion with viscosity being highly dependent on the shear rate (Laurent, supra). This could theoretically cause problems in the microcirculation, where the increased viscosity associated with low shear rates could induce stasis and sludging within vessels (Replogle et al., *Circulation* 36:148, 1967). However, evidence of this was not seen in this study, with at least indirect measurements of microcirculatory function (renal and liver function indices) remaining unchanged by the HA infusion.

EFFECTS OF TIME AND TREATMENT AND INTERACTION BETWEEN TIME AND TREATMENT

1. Parameters measured up to 6 hours post-infusion Pre, 0.5, 1, 4, 6 (hours)

Hemodynamics, blood gases and pH, carbon monoxide, methemoglobin, electrolytes, saline transfused, and urine output

| Parameters | Analysis of variance Volume Infused: 2.5% | | |
|---|---|---|---|
| | Effect of time | Effect HA treatment | Interaction of HA (treatment) over time |
| Heart Rate | .0348 | NS | NS |
| MAP | NS | NS | NS |
| CVP | NS | NS | NS |
| MPA | .0292 | NS | NS |
| MPAW | .0003 | NS | NS |
| Cardiac Output | | | |
| Respiration | | | |
| Arterial pH | NS | NS | NS |
| Arterial pCO2 | .0149 | NS | NS |
| Arterial pO2 | NS | NS | NS |
| Venous pH | NS | NS | NS |
| Venous pCO2 | .0539 | NS | NS |
| Venous pO2 | .0213 | NS | NS |
| Arterial O2 Saturation | NS | NS | NS |
| Venous O2 Saturation | .0003 | NS | NS |
| Arterial O2 Content | .0021 | NS | NS |
| Venous O2 | .0003 | NS | NS |
| Methemoglobin | NS | .0436* | NS |

| Parameters | Analysis of variance Volume Infused: 2.5% -continued | | |
|---|---|---|---|
| | Effect of time | Effect HA treatment | Interaction of HA (treatment) over time |
| Carbon Monoxide | NS | NS | NS |
| Venous Na+ | | | |
| Venous Cl− | | | |
| Saline Tx | | | |
| Urine Output | .0352 | NS | NS |

2. Parameters measured up to 72 hours post-infusion: Pre, 0.5, 1, 4, 6, 24, 48, 72 (hours)

Skin and core temperatures, bleeding time, viscosity, clotting, oncotic and opsonic proteins, p50, 2,3 DPG, ATP, and plasma hemoglobin.

| Parameters | Effect of time | Effect HA treatment | Interaction of HA (treatment) over time |
|---|---|---|---|
| Skin temp | .0001 | NS | NS |
| Core temp | .0001 | NS | NS |
| Bleeding time | .0292 | NS | NS |
| Shed Blood TXB2 | | | |
| Viscosity | .0001 | NS | NS |
| PT | | | |
| PTT | | | |
| Thrombin Time | | | |
| Fibrinogen | | | |
| D-dimer | | | |
| Anti-thrombin III | | | |
| Protein C | | | |
| von Willebrand's | | | |
| Fibronectin | | | |
| TP | | | |
| Albumin | | | |
| p50 | | | |
| 2,3 DPG | | | |
| ATP | | | |
| Plasma hemoglobin | | | |

3. Parameters measured up to 28 days post-infusion: Pre, 0.5, 1, 4, 6, 24, 48, 72, 168, 336, 504, 672 (hours).

| Parameters | Effect of time | Effect HA treatment | Interaction of HA (treatment) over time |
|---|---|---|---|
| Serum BUN | | | |
| Serum creatinine | | | |
| Serum SGPT | | | |
| Serum SGOT | | | |
| Serum LDH | | | |
| Hct | .0001 | NS | NS |
| Hb | .0001 | NS | NS |
| RBC | .0001 | NS | NS |
| WBC | .0001 | NS | NS |
| Platelet Count | .0001 | NS | .0146 |
| Mean platelet volume | .0001 | NS | NS |

EFFECTS OF TIME AND TREATMENT AND INTERACTION BETWEEN TIME AND TREATMENT

1. Parameters measured up to 6 hours post-infusion Pre, 0.5, 1, 4, 6 (hours)

Hemodynamics, blood gases and pH, carbon monoxide, methemoglobin, electrolytes, saline transfused, and urine output.

| | Analysis of variance Volume Infused: 5% | | |
|---|---|---|---|
| Parameters | Effect of time | Effect HA treatment | Interaction of HA (treatment) over time |
| Heart Rate | .0371 | NS | NS |
| MAP | .0111 | NS | NS |
| CVP | .0053 | NS | NS |
| MPA | NS | NS | NS |
| MPAW | .0030 | NS | NS |
| Cardiac Output | | | |
| Respiration | | | |
| Arterial pH | NS | NS | NS |
| Arterial pCO2 | NS | NS | NS |
| Arterial pO2 | NS | NS | NS |
| Venous pH | NS | NS | NS |
| Venous pCO2 | NS | NS | NS |
| Venous pO2 | NS | NS | .0463 |
| Arterial O2 Saturation | NS | NS | NS |
| Venous O2 Saturation | NS | NS | NS |
| Arterial O2 Content | .0029 | NS | NS |
| Venous O2 | .0105 | NS | NS |
| Methemoglobin | NS | .0459* | NS |
| Carbon Monoxide | NS | NS | NS |
| Venous Na+ | | | |
| Venous Cl– | | | |
| Saline Tx | | | |
| Urine Output | .0352 | NS | NS |

2. Parameters measured up to 72 hours post-infusion: Pre, 0.5, 1, 4, 6, 24, 48, 72 (hours)

Skin and core temperatures, bleeding time, viscosity, clotting, oncotic and opsonic proteins, p50, 2,3 DPG, ATP, and plasma hemoglobin.

| Parameters | Effect of time | Effect HA treatment | Interaction of HA (treatment) over time |
|---|---|---|---|
| Skin temp | .0001 | NS | NS |
| Core temp | .0006 | NS | NS |
| Bleeding time | .0181 | NS | NS |
| Shed Blood TXB2 | | | |
| Viscosity | .0001 | NS | NS |
| PT | | | |
| PTT | | | |
| Thrombin Time | | | |
| Fibrinogen | | | |
| D-dimer | | | |
| Anti-thrombin III | | | |
| Protein C | | | |
| von Willebrand's | | | |
| Fibronectin | | | |
| TP | | | |
| Albumin | | | |
| p50 | | | |
| 2,3 DPG | | | |
| ATP | | | |
| Plasma hemoglobin | | | |

3. Parameters measured up to 28 days post-infusion: Pre, 0.5, 1, 4, 6, 24, 48, 72, 168, 336, 504, 672 (hours).
Renal, liver and hematologic parameters.

| Parameters | Effect of time | Effect HA treatment | Interaction of HA (treatment) over time |
|---|---|---|---|
| Serum BUN | | | |
| Serum creatinine | | | |
| Serum SGPT | | | |
| Serum SGOT | | | |
| Serum LDH | | | |
| Hct | .0001 | NS | NS |
| Hb | .0001 | NS | NS |
| RBC | .0001 | NS | NS |
| WBC | .0001 | NS | NS |
| Platelet Count | .0001 | NS | NS |
| Mean platelet volume | .0004 | NS | NS |

EFFECTS OF TIME AND TREATMENT AND INTERACTION BETWEEN TIME AND TREATMENT

1. Parameters measured up to 6 hours post-infusion Pre, 0.5, 1, 4, 6 (hours)

Hemodynamics, blood gases and pH, carbon monoxide, methemoglobin, electrolytes, saline transfused, and urine output.

| | Analysis of variance Volume Infused: 10% | | |
|---|---|---|---|
| Parameters | Effect of time | Effect HA treatment | Interaction of HA (treatment) over time |
| Heart Rate | 0.0127* | 0.5810 | 0.3410 |
| HAP | 0.0057* | 0.7820 | 0.0029* |
| CVP | 0.343 | 0.6490 | 0.1488 |
| MPA | 0.0677 | 0.3870 | 0.6271 |
| MPAW | 0.0041* | 0.0260* | 0.2721 |
| Cardiac Output | 0.8612 | 0.1295 | 0.0006* |
| Respiration | 0.0072* | 0.9395 | 0.1333 |
| Arterial pH | 0.8287 | 0.2338 | 0.9926 |
| Arterial pCO2 | 0.0257* | 0.3454 | 0.7003 |
| Arterial pO2 | 0.4271 | 0.3423 | 0.7644 |
| Venous pH | 0.3598 | 0.7703 | 0.8216 |
| Venous pCO2 | 0.0073* | 0.5153 | 0.8591 |
| Venous pO2 | 0.0114* | 0.2904 | 0.0214* |
| Arterial O2 Saturation | 0.0003* | 0.1678 | 0.0050* |
| Venous O2 Saturation | 0.0020* | 0.2671 | 0.0135* |
| Arterial O2 Content | 0.0032* | 0.5343 | 0.4442 |
| Venous O2 | 0.0001* | 0.6279 | 0.1254 |
| Methemoglobin | 0.0001* | 0.0317* | 0.0001* |
| Carbon Monoxide | 0.0060* | 0.7206 | 0.2626 |
| Venous Na+ | 0.0044* | 0.9120 | 0.3206 |
| Venous Cl– | 0.2386 | 0.9302 | 0.9587 |
| Saline Tx | 0.0001* | 0.1545 | 0.3500 |
| Urine Output | 0.0203* | 0.7612 | 0.0473* |

2. Parameters measured up to 72 hours post-infusion: Pre, 0.5, 1, 4, 6, 24, 48, 72 (hours)

Skin and core temperatures, bleeding time, viscosity, clotting, oncotic and opsonic proteins, p50, 2,3 DPG, ATP, and plasma hemoglobin.

| Parameters | Effect of time | Effect of HA treatment | Interaction of HA (treatment) over time |
|---|---|---|---|
| Skin temp | 0.0001* | 0.8369 | 0.1373 |
| Core temp | 0.2120 | 0.7787 | 0.8103 |
| Bleeding time | 0.0003* | 0.0062* | 0.0001* |
| Shed Blood TXB2 | 0.1601 | 0.5342 | 0.8583 |
| Viscosity | 0.0001* | 0.0194* | 0.0002* |
| PT | 0.0521 | 0.7337 | 0.2202 |
| PTT | 0.0033* | 0.7588 | 0.4737 |
| Thrombin Time | 0.0001* | 0.9433 | 0.5124 |
| Fibrinogen | 0.0001* | 0.4573 | 0.0673 |
| D-dimer | 0.0005* | 0.5221 | 0.1635 |
| Anti-thrombin III | 0.0004* | 0.6052 | 0.1895 |
| Protein C | 0.7756 | 0.7879 | 0.0084* |
| von Willebrand's | 0.0535 | 0.7926 | 0.0112* |
| Fibronectin | 0.0208* | 0.3894 | 0.5720 |
| TP | 0.0001* | 0.0754 | 0.6677 |
| Albumin | 0.0899 | 0.3915 | 0.2630 |
| p50 | 0.0316* | 0.1838 | 0.2080 |
| 2,3 DPG | 0.0019* | 0.2292 | 0.1166 |
| ATP | 0.1202 | 0.2661 | 0.0888 |
| Plasma hemoglobin | 0.3590 | 0.7592 | 0.7843 |

3. Parameters measured up to 28 days post-infusion: Pre, 0.5, 1, 4, 6, 24, 48, 72, 168, 336, 504, 672 (hours).

Renal, liver and hematologic parameters.

| Parameters | Effect of time | Effect of HA treatment | Interaction of HA (treatment) over time |
|---|---|---|---|
| Serum BUN | 0.9810 | 0.9662 | 0.0011* |
| Serum creatinine | 0.1927 | 0.8304 | 0.1944 |
| Serum SGPT | 0.0001* | 0.5060 | 0.8706 |
| Serum SGOT | 0.0001* | 0.8115 | 0.8173 |
| Serum LDH | 0.0001* | 0.7189 | 0.5675 |
| Hct | 0.0001* | 0.0974 | 0.7221 |
| Hb | 0.0001* | 0.0351* | 0.9951 |
| RBC | 0.0001* | 0.6320 | 0.5396 |
| WBC | 0.0001* | 0.8738 | 0.8379 |
| Platelet Count | 0.0001* | 0.0240* | 0.2245 |
| Mean platelet volume | 0.0001* | 0.7362 | 0.1315 |

The Role of HA in Platelet Interaction

For adhesion to occur, the platelet must contact the vessel wall and then spread onto components of the subendothelial matrix. The platelet surface membrane has adhesion receptors that bind to specific matrix molecules. These receptors include the glycoprotein (gp)Ib-IX complex, a receptor for subendothelial von Willebrand factor, and several of the membrane glycoproteins of the integrin superfamily of adhesion receptors: gpIa/IIa (a collagen receptor), gpIc/IIa (a fibronectin receptor), gpIc'/IIa (a laminin receptor), and $\alpha_v\beta_3$ (a vitronectin receptor). In addition, many components of the matrix, such as von Willebrand factor, thrombospondin, fibronectin, and collagen, can interact with one another as well as with platelets. Once activation has occurred, another platelet-membrane integrin, gpIIb/IIIa, becomes competent to bind von Willebrand factor and fibronectin and is involved in the spreading of platelets on the subendothelial matrix.

Ristocetin is an agent which specifically promotes platelet aggregation by inducing the monophasic agglutination reaction of vWF binding to the glycoprotein 1b receptor on platelets. After vWF binds to gpIb, the platelets release ADP and serotonin, both which are effective platelet aggregating agents. Thus, we investigated the effect of HA on platelet aggregation mediated by von Willebrand factor binding to the platelet gpIb receptor in the following experiment.

Platelet aggregation was performed using a Series 1000B Payton Scientific Lumi-Aggregometer as follows. Platelet-rich-plasma (PRP) was prepared from fresh whole blood anticoagulated with sodium citrate by centrifuging it for 10 minutes at 200×g and removing the upper PRP layer. The PRP was adjusted to 300,00/μl with platelet-poor-plasma (prepared by centrifuging the blood a second time at 100×g for 10 minutes). To 400 μl of PRP was added 50 μl of 0.4% w/w HA solution (molecular weight $2.2 \times 10^6$, 10% final concentration) or, PBS carrier buffer. After a 5 minute incubation at 37° C., 50 μl of 12 mg/mL ristocetin (Bio/Data Corp) were added to induce the aggregation reaction (mediated by platelet gpIb receptor and plasma vWF). Changes in sample light transmittance was monitored for 5 minutes after addition of ristocetin. Initial rate is the maximum slope of agglutination obtained during the first minute.

Figure 12A:
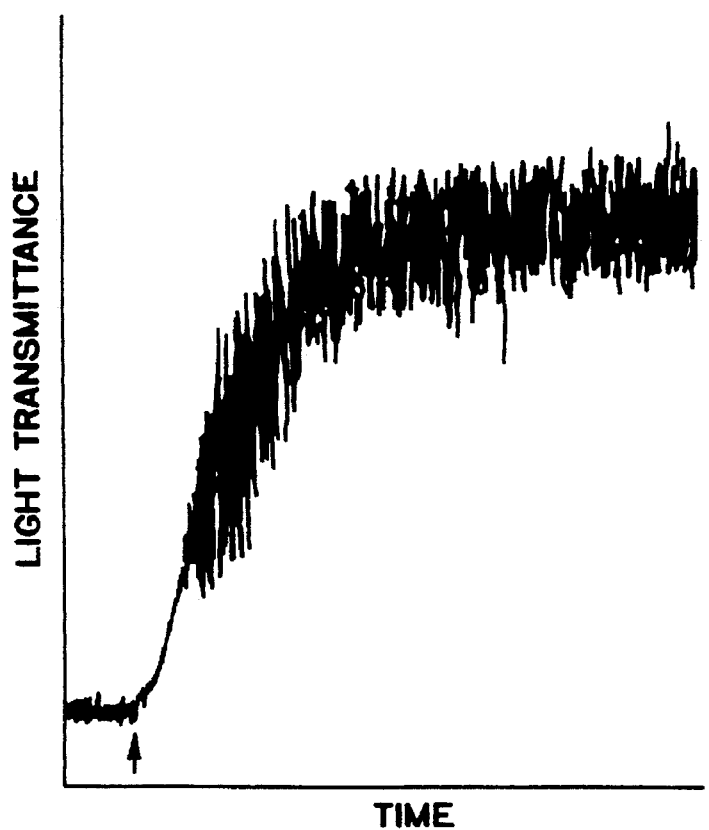
FIGS. 12A and 12B illustrate spectrometric measurement of the light transmittance of platelet samples treated with a PBS control (FIG. 12A) or 10% HA (FIG. 12B) in a ristocetin induced platelet aggregation assay.
Figure 12B:
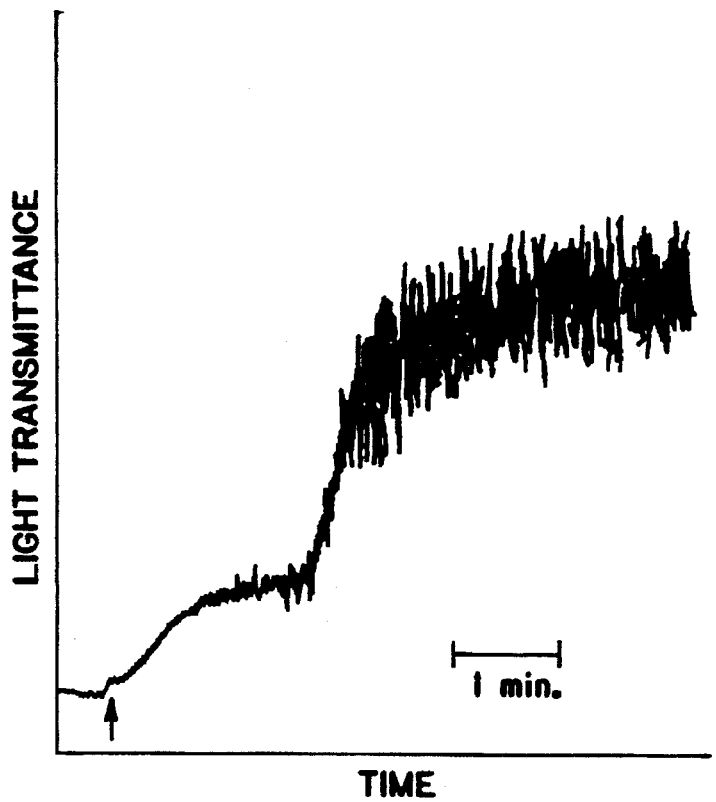

The slope of the agglutination reaction and the biphasic shape of the aggregation curve (FIG. 12) shows that HA inhibited platelet aggregation induced by the vWF and platelet gpIb receptor interaction.

A second experiment was performed to determine if the inhibition of vWF-gpIb induced platelet aggregation was specific for HA. We therefore compared HA to another polyanionic polysaccharide, carboxymethylcellulose (CMC). Two CMC solutions were tested in this study. Solution CMC-1 was 0.7% CMC (lot 7H3SF) at apparent viscosity=350 centipoise ($2.2 \, \text{sec}^{-1}$). Solution CMC-2 was 2% CMC (7MFPH) at apparent viscosity=350 centipoise ($2.2 \, \text{sec}^{-1}$). The CMC solutions were prepared to approximately the same viscosity as the HA solution and compared for ristocetin aggregation as described in the above example. The amount of platelet aggregation induced by ristocetin was significantly less with HA treatment as compared to CMC (FIG. 13) indicating that the effect of HA on platelet aggregation is not related to the general viscosity of the polyanionic solution but is specific for HA.

Previous studies have reported that pigs with von Willebrand disease which were subjected to coronary vessel stenosis by an external ring did not develop vascular occlusion in contrast with normal animals (Nichols et al., *Circ. Res.* 59:15, 1986; Badimon et al. (*Circulation* 78:1431, 1998) further reported that the absence of vWF in both heparinized and nonanticoagulated blood significantly reduces platelet thrombus formation at high local wall shear rates (stenotic or microcirculatory flow), and also demonstrated a considerably greater reduction in platelet deposition compared with anticoagulation with heparin. They concluded that it is likely that vWF plays a significant role in the thrombotic complications associated with stenotic cardiovascular disease and that the acute thrombotic response may be more sensitive to manipulation of vWF that of other factors.

Accordingly, our demonstration that HA specifically interferes with the function of vWF establishes the therapeutic importance of HA in treating thrombotic conditions which are, or are at risk of becoming, life threatening.

USE

Compositions for administration according to the invention comprise a solution of HA dissolved or suspended in an acceptable carrier, preferably an aqueous carrier. A variety of aqueous carriers may be used, e.g. water, buffered 0.9% saline and the like. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Administration may be either by intermittent injections, for example, into an indwelling intravenous cannula or by pump-driven infusion at a constant rate. The exact effective dosage varies with the patient's weight and may be influenced by a number of factors, including the route of administration, type and state of disease, and overall health status of the particular patient.

More specifically, HA can be used to prevent platelet adhesion and subsequent aggregation to a damaged vessel wall caused by any of the medical conditions mentioned herein. This can be accomplished, for example, by infusing a 0.4% HA solution, preferably in a physiological buffer, into the circulation remote from the endothelial damage, through a standard means such as by an intravenous or intraarterial catheter. The HA solution would be administered in an amount greater than 5% of the patient's blood volume, or preferably 10% of the patients blood volume.

Alternatively, the HA could be administered directly to the site of endothelial damage. One method by which this can be accomplished is by placing a catheter directly at the site of endothelial cell damage and slowly administering the HA proximal to the site of damage. In this case an effective dose of HA solution would be less than that required when administering the solution remote from the site of endothelial cell damage.

A specific example of the latter is the prevention of platelet adhesion to damaged endothelium caused by percutaneous transluminal coronary angioplasty (PTCA). In this procedure a balloon catheter is placed into a coronary artery that is partially occluded. The balloon is inflated to expand the inner diameter of the artery, thus improving blood flow through the vessel. This procedure often damages the endothelium of the artery which leads to undesired deposition of circulating blood cells on the damaged vessel wall. Cells which adhere to the vessel wall include platelets, white blood cells, and granulocytes. Following inflation of the balloon and prior to removing the catheter, HA solution of 0.1% to 5% is infused through the catheter just proximal from the site of angioplasty in order to interfere with platelet or granulocyte adherence to the damaged vessel wall. By reducing the adherence of these cells to the vessel wall the vessel patency is maintained and vessel reocclusion is reduced or prevented.

The use of HA solution in this way can be also applied following artherotomy, which also damages the vessel wall and thus causes platelet deposition, thrombosis, and reocclusion.

HA can also be used to prevent or reduce platelet adhesion to vascular prostheses such as collagen or synthetic vascular grafts, natural or synthetic heart valves, vascular stents, and other blood contacting products and materials such as blood dialysis membranes, catheters, tubing, etc. Prevention of platelet adherence to these substrates is accomplished by coating HA, or its derivatives, to the surface of the prosthetic or blood contacting material which will be in contact with the blood using standard techniques. Upon exposure to blood, platelets will be less likely to adhere to the surface compared to non-HA coated surfaces. The efficacy of any device may be tested prior to use by standard cell adhesion assays well known to those skilled in the art. For example, a small sample containing a platelet suspension is incubated with a concentration of HA or device coated with HA at physiological temperature, and then, for example, by placing the sample in a Neubauer chamber and evaluating the percentage of platelets found in aggregates of two or more by light microscopy (or alternatively by percentage of platelets bound to the surface of the device to be examined).

Other Embodiments

From the above description, one skilled in the art can easily ascertain the essential characteristics of the present invention, and without departing from the spirit and scope thereof, can make various changes and modifications of the invention to adapt it to various usages and conditions.

For example, homologues, analogues, derivatives and complexes of HA which are capable of inhibiting the action of vWF may also be used in the methods of the invention (e.g., Balasz, U.S. Pat. No. 4,582,865; De Belder PCT Publication No. WO 86/00912; Malson et al., PCT Publication No. 84/20560; Prestwich et al., EP Publication No. 0416250A2; Hamilton et al., U.S. Pat. No. 4,937,270; and Burns et al., U.S. Pat. No. 5,017,229); any particular compound of HA may be tested for efficacy according the methods described herein.

In addition, the invention also includes the use of HA and its chemically modified derivatives to deliver therapeutic drugs directly to sites where platelets have already adhered. For example drugs can be incorporated into the HA by admixing or by immobilizing the drug by chemical attachment to the HA molecule or by ionic interaction between the drug and HA (e.g., see Sparer et al., 1983, Chapter 6, pp. 107–119, In *Controlled Release Delivery Systems,* Roseman et al. (ed), Marcel Dekker, Inc.: New York). The HA-drug complex, or HA derivative complex can then bind to the vWF and deliver the drug in a site specific manner to the platelet or to the damaged vessel wall. A specific example is to mix the tissue plasminogen activator (tPA) with HA in a therapeutic dose and to infuse the HA as described in the above example. The HA will target the tPA directly to the platelets in blood clots and thereby deliver the drug site specifically where it must act.

What is claimed is:

1. A method of treating a thrombotic condition in a mammal, said method comprising the intravenous administration to said mammal of a therapeutic composition consisting essentially of hyaluronic acid, or salts thereof, in a dosage effective to inhibit the adherence and aggregation of platelets.

2. The method of claim 1, wherein said thrombotic condition is venous thrombosis.

3. The method of claim 2, wherein said mammal is pregnant.

4. The method of claim 1, wherein said thrombotic condition is arterial thrombosis.

5. The method of claim 4, wherein said thrombotic condition is coronary artery thrombosis.

6. A method of preventing the formation of a thrombus in a mammal at risk of developing thrombosis, said method comprising the intravenous administration to said mammal of a therapeutic composition consisting essentially of hyaluronic acid, or salts thereof, in a dosage effective to inhibit the adherence and aggregation of platelets.

7. The method of claim 6, wherein said mammal is at increased risk of developing a thrombus due to a medical condition which disrupts hemostasis.

8. The method of claim 7, wherein said medical condition is heparin induced thrombocytopenia.

9. The method of claim 7, wherein said medical condition is coronary artery disease.

10. The method of claim 7, wherein said medical condition is atherosclerosis.

11. The method of claim 6, wherein said mammal is at increased risk of developing a thrombus due to a medical procedure.

12. The method of claim 11, wherein said medical procedure is cardiac surgery.

13. The method of claim 12, wherein said medical procedure is a cardiopulmonary bypass.

14. The method of claim 11, wherein said medical procedure is a catheterization.

15. The method of claim 14, wherein said catheterization is cardiac catheterization.

16. The method of claim 15, wherein said catheterization is percutaneous transluminal coronary angioplasty.

17. The method of claim 11, wherein said medical procedure is atherotomy.

18. The method of claim 11, wherein said medical procedure involves placement of a prosthetic device.

19. The method of claim 18, wherein said prosthetic device is a cardiovascular valve.

20. The method of claim 18, wherein said prosthetic device is a vascular graft.

21. The method of claim 18, wherein said prosthetic device is a stent.

22. The method of claim 1, wherein said HA is administered after treatment with a thrombolytic agent.

23. The method of claim 1, wherein said HA is administered concurrently with a thrombolytic agent.

24. The method of claim 11, wherein said HA is administered during said medical procedure.

25. A method of inhibiting the adherence of platelets to the surface of a prosthetic device comprising coating said device with hyaluronic acid, or salts thereof, in an amount sufficient to inhibit the interaction of said platelets with said surface prior to exposure of said device to said platelets.

26. The method of claim 25, wherein said prosthetic device is synthetic.

27. The method of claim 25, wherein said prosthetic device is bioprosthetic.

28. The method of claim 25, wherein said prosthetic device is a coronary valve.

29. The method of claim 25, wherein said prosthetic device is a stent.

30. The method of claim 27, wherein said prosthetic device is a vascular graft.

31. The method of claims 1, 6, or 25, wherein said HA is capable of inhibiting platelet adherence and aggregation associated with the interaction of von Willebrand factor with said platelets.

32. The method of claim 1 or 6 wherein the hyaluronic acid is administered in a dosage in the range of about 5% to about 15% of the total blood volume of the mammal.

* * * * *

UNITED STATES PATENT AND TRADEMARK OFFICE
CERTIFICATE OF CORRECTION

PATENT NO.   : 5,585,361
DATED        : December 17, 1996
INVENTOR(S)  : James W. Burns and Cesare R. Valeri It is certified that error appears in the above-identified patent and that said Letters Patent is hereby corrected as shown below:

Column 3,
Line 28, delete "of yon Willebrand" and insert -- of von Willebrand --.

Column 12,
Line 37, delete "HAP" and insert -- MAP --.

Column 18,
Line 21, delete "of claim 27" and replace with -- of claim 25 --.

Signed and Sealed this

Twenty-second Day of March, 2005

JON W. DUDAS
*Director of the United States Patent and Trademark Office*